United States Patent
Mikhail

[11] Patent Number: 5,197,986
[45] Date of Patent: Mar. 30, 1993

[54] RECESSED PATELLAR PROSTHESIS

[76] Inventor: W. E. Michael Mikhail, 4203 Shamley Green, Toledo, Ohio 43623

[21] Appl. No.: 599,432

[22] Filed: Oct. 18, 1990

Related U.S. Application Data

[63] Continuation-in-part of Ser. No. 508,088, Apr. 11, 1990, abandoned.

[51] Int. Cl.$^5$ .............................................. A61F 2/38
[52] U.S. Cl. ..................................................... 623/20
[58] Field of Search ........................ 623/20, 18, 16, 21

[56] References Cited

U.S. PATENT DOCUMENTS

| | | | |
|---|---|---|---|
| 3,765,033 | 10/1973 | Goldberg et al. | 623/20 |
| 3,878,566 | 4/1975 | Bechtol | 623/20 |
| 4,081,866 | 4/1978 | Upshaw et. al. | 623/20 |
| 4,158,894 | 6/1979 | Worrell | 623/20 |
| 4,276,660 | 7/1981 | Laure | 623/21 |
| 4,462,120 | 7/1984 | Rambert et al. | 623/20 |
| 4,822,366 | 4/1989 | Bolesky | 623/20 |

OTHER PUBLICATIONS

"Patellar Prosthesis Positioning in Total Knee Arthroplasty" by Luis S. J. Gomes et al, *Clinical Orthopaedics and Related Research,* Nov. 1988, pp. 72–81.
Catalog of Dow Corning Wright, Arlington, Tenn., copyright 1989 entitled "Whiteside ORTHOLOC® Modular Knee System".
Catalog of Intermedics Orthopedics, Inc. Austin, Tex., copyright 1987 entitled "The Intermedics Natural-Knee® System with Cancellous-Structured Titanium TM".
Catalog of DePuy, Warsaw, Ind., division of Boehringer Mannheim Corporation, copyright 1988, entitled "The AMK TM Total Knee System-Design Rationale and Surgical Procedure", pp. 13 and 47.
Catalog of Biomet, Inc., Warsaw, Ind., entitled "AGC Total Knee System-Patellar Femoral Systems".

*Primary Examiner*—Randall L. Green
*Assistant Examiner*—Mary Beth O. Jones
*Attorney, Agent, or Firm*—Emch, Schaffer, Schaub & Porcello Co.

[57] ABSTRACT

A patellar prosthesis for use in combination with a prepared patella is provided having a dome, a body portion and a post with longitudinal grooves.

19 Claims, 3 Drawing Sheets

RECESSED PATELLAR PROSTHESIS

CROSS REFERENCE TO RELATED APPLICATION

This is a continuation-in-part of application Ser. No. 07/508,088 filed Apr. 11, 1990, now abandoned.

BACKGROUND OF THE INVENTION

In total knee arthroplasty it is customary to resurface the articulating ends of the femur and the tibia with prostheses which are fastened to the cut and prepared ends of the femur and tibia. One such prosthesis is that described in a catalog published by Johnson & Johnson Orthopaedics Inc. entitled "P. F. C. Total Knee System" ("P.F.C. is a registered trademark of Johnson & Johnson Orthopaedics Inc.) using a surgical technique described in a booklet published by Johnson & Johnson Products Inc. entitled "Surgical Technique—The Press Fit Condylar Total Knee System with Specialist Instruments." Another such prosthesis is described in U.S. Pat. No. 4,822,366.

One component of the P.F.C. Total Knee System and virtually every other total knee replacement system utilized is a patellar component.

Heretofore great difficulty has been encountered in providing a patellar component which will endure, for extended periods of time, the rigors to which such components are placed. Thus, a patellar component is subjected to continual rubbing against the femoral component of the prosthesis with each flexing movement of the leg. As a result, the patellar component may wear to an extent as to impede function of the knee even though the other components may not be worn out. In addition, it may also cause undue wear on the other components of a total knee system.

In a total knee system, the patellar component is typically a dome-shaped member which is implanted on a flat surface or a recess cut into the patient's patella. The patellar implant may either be all plastic, typically high molecular weight polyethylene (HMWPE) or plastic with a metal backing formed of titanium, chrome-cobalt alloy, stainless steel or the like.

In addition to the patellar implant shown in the Johnson & Johnson Orthopaedics brochure entitled "P.F.C. Total Knee System", other types of patellar implants are disclosed in catalogs published by Dow Corning Wright entitled "Whiteside Ortholoc Modular Knee System" and published by De Puy, Warsaw, Indiana, a Division of Boehringer Mannheim Corporation, entitled "The AMK Total Knee System".

As will be appreciated, it is desirable to utilize a patellar implant which combines the advantages of requiring a minimal amount of cutting of the patella, secure placement of the patellar implant and the ability to easily remove such implant in the event revision is required.

Accordingly, it is an object of the present invention to provide a patellar prosthesis for use in combination with the prepared patella bed in which minimal amount of the patient's natural patella is required to be removed.

It is a further object of the present invention to provide a patellar prosthesis designed for implantation in a patella which can be replaced with minimal damage to the patella in the event revision is required.

SUMMARY OF THE INVENTION

The present invention relates to a new and improved patellar implant formed completely from plastic having a domed portion intended to face outwardly from the patella for engagement with the condylar or trochlear groove of a femoral prosthesis component, a body portion and a central post extending from said body portion away from the domed portion and intended to be fixedly secured within a recess cut into the patella, said post having a plurality of longitudinal grooves to ensure proper fixation.

DETAILED DESCRIPTION OF THE INVENTION

Figure 1:
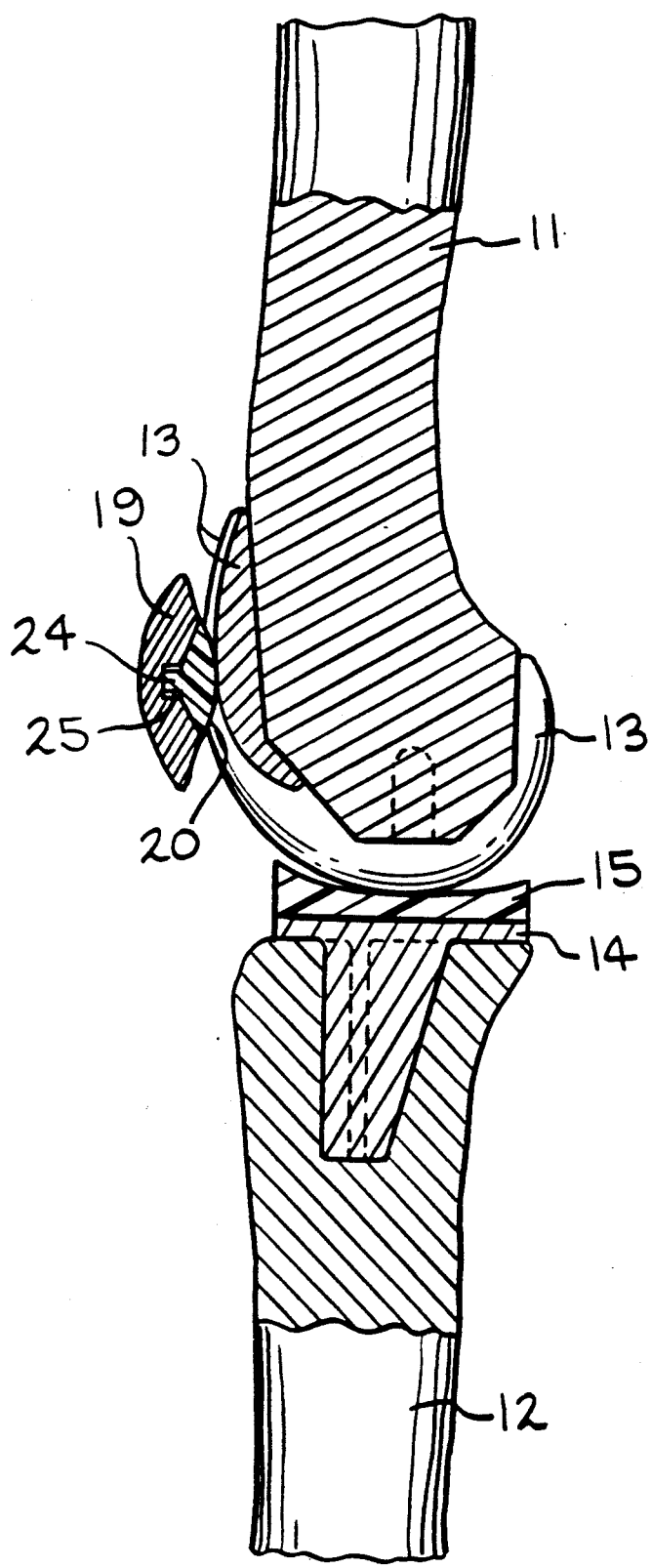
FIG. 1 is a schematic view partly in section of a total knee system implanted in the leg of a patient and showing specifically the position of the patella with the patellar implant of the present invention articulating with the femoral component of the implant.

Referring now to the drawings, there is shown in FIG. 1, a leg including the femur 11 and tibia 12 to which a total knee prosthesis has been implanted including a femoral implant 13, a tibial base implant 14 and a tibial insert 15. Typically, the femoral implant 13 and tibial base implant 14 are formed of metal such as titanium alloy or chrome-cobalt while the tibial insert 15 is formed of plastic such as high molecular weight polyethylene (HMWPE).

There is also shown a patella 19 having implanted therein a patellar implant generally designated by the number 20 of the present invention.

In the embodiment disclosed in FIGS. 1, 2, 3 and 5-7, the patellar implant 20 is formed as a unitary body and includes a dome-shaped portion 21, facing outwardly for engagement with the femoral implant 13.

Figure 5:
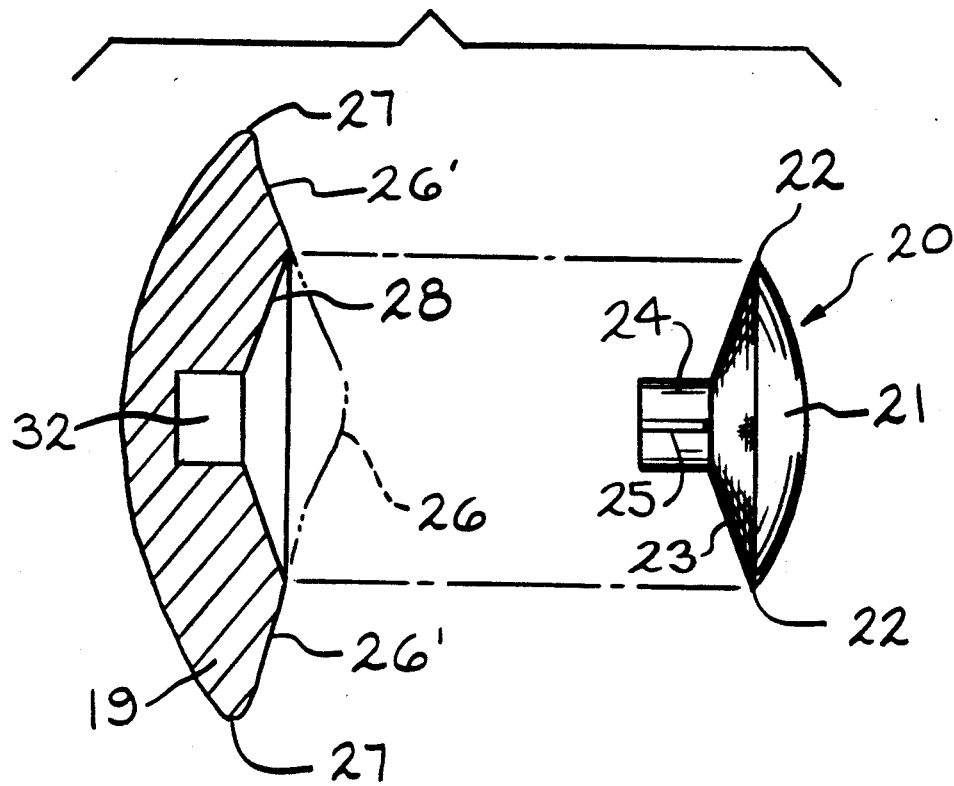
FIG. 5 is a view showing schematically a patella in section following osteotomy to prepare it for receiving the implant of the present invention and showing, removed therefrom, the patellar implant of the present invention.
Figures 6, 7:
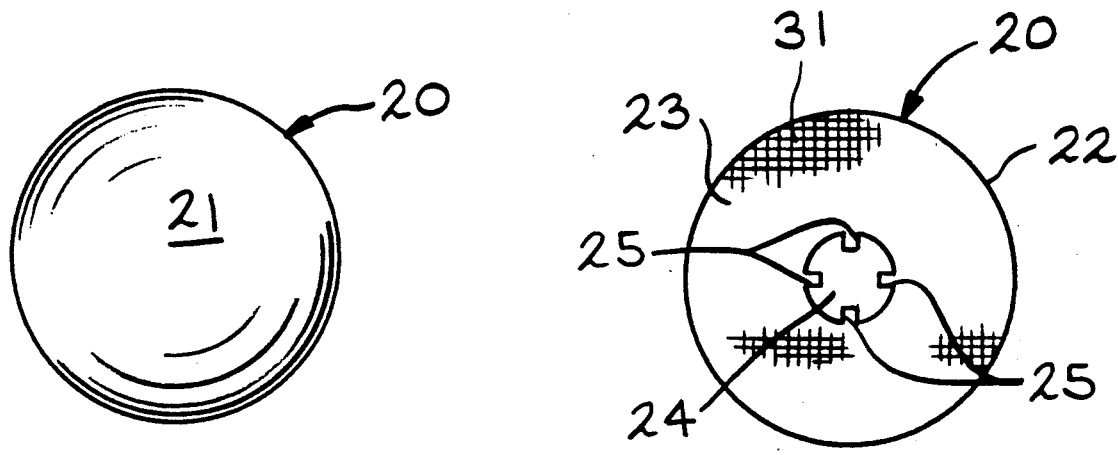
FIG. 6 is a top plan view of the patellar implant of the present invention.
FIG. 7 is a bottom view of the patellar implant of the present invention showing the post including the longitudinal grooves.

As can be seen in FIG. 5, the patella 19, prior to osteotomy to prepare it to receive the patellar implant 20, included a natural dome 26 which must be removed. Some resection procedures require that the entire dome 26 be removed completely to the peripheral edge 27. Others require that only the central portion of the dome 26 be removed. A major advantage of the patellar implant 20 of the present invention is that it may be implanted with a minimal amount of bone removed from the patella 19. Thus, the patella 19 is prepared to receive the patellar implant 20 so as to leave intact the outer portions 26' of the dome 26 of the patella 19.

Figure 3:
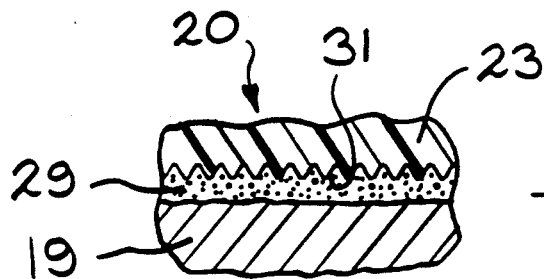
FIG. 3 is a sectional view taken through line 3—3 of FIG. 2.

The dome 21 of the patellar implant 20 has a peripheral edge 22 which, upon implantation is to meet smoothly with the outer portion 26' of the patella 19. Tapering inwardly from the peripheral edge 22 in a direction away from the dome 21 is a conical-shaped body portion 23 from which a central post 24 extends. The post 24 has a plurality of longitudinal grooves 25. As can be seen in FIG. 3, the patellar implant 20 is retained in the prepared patella 19 by polymethylmethacrylate (PMMA) cement 29 or other suitable bone cement. Preferably, the surface of the conical tapered body portion 23 is formed with a roughened, grooved or waffle type surface 31 to enhance retention with the PMMA cement 29.

In the osteotomy to prepare it, the patella 20 has cut therein a cavity including a first conical-shaped section 28 slightly sized and shaped to receive the conical-shaped body portion 23 of the patellar implant 20 so that the peripheral edge 22 of the dome 21 will meet smoothly with the remaining upper surface of the outer portion 26' of the patella dome.

The cavity also includes a lower cylindrical section 32 having a diameter slightly larger than the diameter of the post 24 and a depth slightly greater than the length of the post 24.

Immediately prior to implantation of the patellar implant 20, a suitable quantity of PMMA cement is placed in the cavity sections 28 and 32 and the patellar implant 20 is then forced into such cavity sections with the PMMA cement being, in effect, compression molded around the post 24, into the grooves 25 and along the face 23 of the conical body including the waffle surface 31 to firmly retain the patellar implant 20 therein. As will be appreciated, the presence of the grooves 25 in the stem 24 retained firmly by the PMMA cement serves to rotationally fix the patellar implant 20 in place.

In the event it is required to replace the patellar implant 20, it will be possible to drill a passageway into the solid post 24 in order to provide means to engage a retriever instrument to such patellar implant 20. In this way the patellar implant 20 may be removed with minimal damage to the patella 19. As will be appreciated, the presence of the conical tapered surface on the body portion 23 will permit easier removal and yet will provide suitable retention within the conical-shaped cavity 28 to provide good fixation when combined with the fixation of the post 24 in the cylindrical section 32. As previously mentioned, significant advantage of the patellar implant 20 shown in FIG. 2 over the prior art resides in the fact that, by virture of the tapered surface, a smaller amount of bone material is removed from the patella 19 without compromising the sound fixation of the patellar implant 20.

Figure 4:
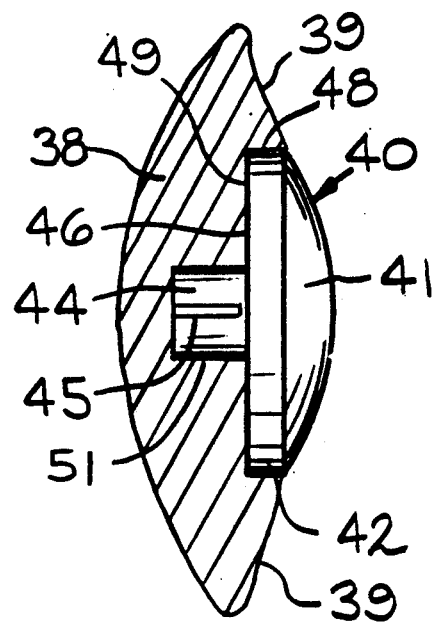
FIG. 4 is a view similar to the view of FIG. 2 showing a modified patellar implant.
Figure 2:
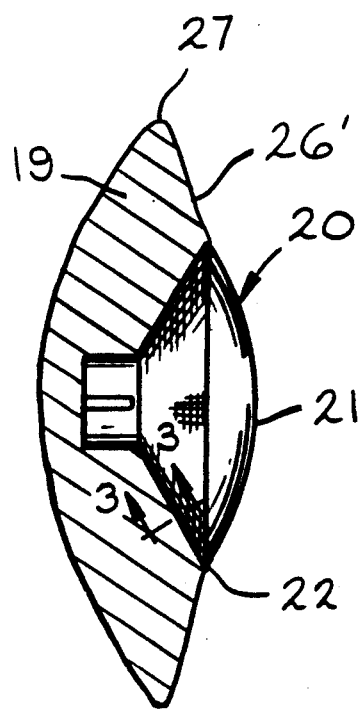
FIG. 2 is a view of one embodiment of the present invention showing the patellar implant of the present invention implanted in a patella.

Referring now to FIG. 4, there is provided a modified patellar implant 40 secured to a patella 38 which has been prepared specifically to receive it. The modified patellar implant 40 has a dome 41 facing outwardly for engagement with the femoral implant 13 similar to the dome 21 of the previous embodiment. As in the previous embodiment, the patella 38 is prepared to receive the implant in such manner as to leave the outer portions of the dome 39 intact. The patellar implant 40 includes a short cylindrical body section 42 extending from the dome-shaped portion 41 and a central post 44 depending from the cylindrical section 42. The post 44 has a plurality of longitudinal grooves 45, preferably three or four in number. The cylindrical body section 42, opposite the dome-shaped portion 41, has a generally planar face 46 from which the post 44 extends. Preferably the planar face 46 is roughened or formed with a series of ridges or grooves in a waffle or other configuration to enhance bonding.

In the osteotomy to prepare it, the patella 39 has drilled therein a cavity including a first cylindrical-shaped section 48 slightly larger in diameter than the diameter of the cylindrical section 42 of the patellar implant 40 and having a depth substantially equal to the height of such cylindrical section 42 so that when the planar bottom face 46 of such cylindrical section 42 rests against the planar face 49 of the first cylindrical-shaped section 42, the peripheral edge of the dome 41 will meet smoothly with the remaining upper surface 39 of the patella dome. The drilled cavity also includes a lower cylindrical section 51 having a diameter slightly larger than the diameter of the post 44 and a depth slightly greater than the length of the post 44.

Immediately prior to implantation of the patellar implant 40, a suitable quantity of PMMA cement is placed in the cavity sections 48 and 51 and the patellar implant 40 is then forced into such cavities with the PMMA cement being, in effect, compression molded around the post 44 and into the grooves 45, along the planar bottom face 46 and around the edge of the cylindrical section 42 to firmly retain the patellar implant 40 therein. As will be appreciated, the presence of the grooves 45 retained by the PMMA cement assists in rotationally fixing the patellar implant 40 in place.

Figure 8:
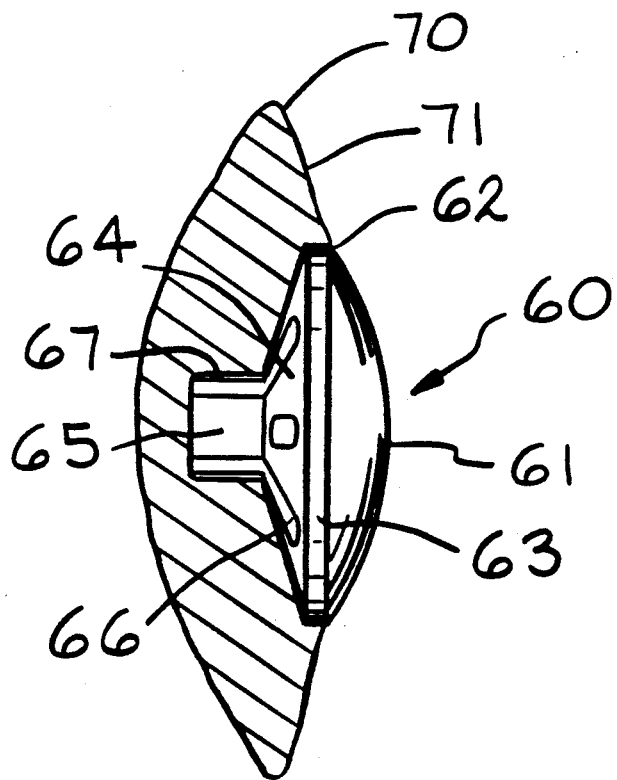
FIG. 8 is a view similar to FIG. 2 showing a further modified patellar implant.
Figure 9:
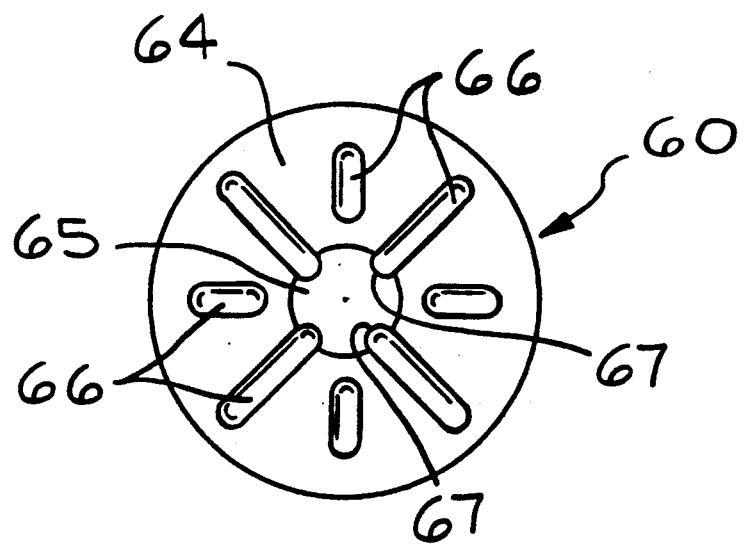
FIG. 9 is a view similar to FIG. 7 showing the further modified patellar implant of FIG. 8.

Referring now to FIGS. 8 and 9, there is provided a further modified patellar implant 60 designed to be secured to a patella 70 having a dome 71 which has been specifically prepared to receive it. This embodiment of the patellar implant 60 has a dome 61 facing outwardly for engagement with the femoral implant 13 similar to the dome 21 of the embodiment shown and described in FIG. 2. The dome 61 extends radially outwardly to a peripheral edge 62 which following implantation, meets the dome 71 of the natural patella 70 in a smooth line of juncture. The patellar implant 60 includes a short cylindrical body section 63 extending from the edge 62 in a direction away from the dome 61 and a conical-shaped body portion 64 tapering away from the dome 61. A central post 65 depends from the conical tapered body portion 64.

Preferably, the surface of the conical tapered body portion 64 has formed therein a plurality of grooves 66 intended to assist in locking the patellar implant 60 firmly in place. Additionally, the post 65 may be provided with a series of longitudinal grooves 67 as in the previous embodiment.

In preparing the patella 70 to receive the patellar implant 60, initially the top of the dome 71 is cute to provide a flat surface. It is not necessary that a large portion of such dome 71 be removed but only enough to provide a flat surface to permit the drill and reamer to be accurately guided. After cutting, the patella 70 is drilled and reamed to provide a cavity shaped to receive the patellar implant 60 so that, with cement placed therein, upon implantation the patellar implant peripheral edge 62 will meet smoothly with the natural patella dome 71.

While the body portion 64 has been described as having a conical-shaped section, it should be understood that other configurations may be utilized provided the surface of such body portion tapers away from the dome 61 thereby insuring that a minimal amount of the human patella 70 is removed in preparing the patellar implant 60 for implantation.

The patellar of the present invention is one which provides superior performance and yet permits ready revision with a minimum of problems.

Many other modifications will become readily apparent to those skilled in the art. Accordingly, the scope of this invention should be limited only by the scope of the appended claims.

I claim:

1. For use in combination with a prepared patella from which the top of its dome has been removed to form a cavity therein, said cavity being incircled by the remaining portion of the surface of said dome, a one piece patellar prosthesis comprising:
   (a) a dome having an outwardly facing surface, convexly curved throughout, positioned for sliding engagement with a femoral prosthesis, said dome terminating at its radial outer extent in a circular edge defining a plane, said dome having a central axis perpendicular to said plane;
   (b) a body having a surface facing away from said outwardly facing surface, said body extending to said circular edge and said body surface having a first central area in proximity to said central axis spaced from said plane by a predetermined amount and other areas extending radially outwardly from said central axis tapering without interruption toward said plane; and
   (c) post means extending from said body surface along said central axis.

2. A patellar prothesis according to claim 1, wherein said body surface has a conical configuration.

3. A patellar prosthesis according to claim 1, wherein said body includes a cylindrical portion extending from said circular edge and joining said body surface.

4. A patellar prosthesis according to claim 1, wherein said post means comprises a central post terminating in a free end, said post having a plurality of longitudinal grooves extending to said free end.

5. A patellar prosthesis according to claim 4, wherein the center of said central post is solid.

6. A patellar prosthesis comprising
   (a) a central post extending along a longitudinal axis and having a plurality of longitudinal grooves and
   (b) a body portion extending from said central post, said body portion having
      (i) a first side extending outwardly from said longitudinal axis and tapering, without interruption away from said central post to an outer peripheral edge; and,
      (ii) a second side having a domed surface, convexly curved throughout, with an apex lying on said longitudinal axis, said apex being spaced axially from said central post further than any other portion of said domed surface.

7. A patellar prosthesis according to claim 6, wherein said outer peripheral edge defines a portion substantially parallel to said extending from said first side to said second side.

8. A patellar prosthesis according to claim 6, wherein said outer peripheral edge defines a circle.

9. A patellar prosthesis according to claim 6, wherein said outer peripheral edge defines a cylindrical portion extending from said first side to said second side surface.

10. A patellar prosthesis according to claim 6, wherein said first side has a conical configuration.

11. For use in combination with a prepared patella from which the top of its dome has been removed to form a cavity therein, said cavity being encircled by the remaining portion of the surface of said dome, a one piece patellar prosthesis comprising:
   (a) a dome having an outwardly facing surface, convexly curved throughout, positioned for sliding engagement with a femoral prosthesis, said dome terminating at its radial outer extend in a circular edge defining a plane, said dome having a central axis perpendicular to said plane;
   (b) a body having a roughened surface facing away from said outwardly facing surface, said body extending to said circular edge and said body surface having a first central area in proximity to said central axis spaced from said plane by a predetermined amount and other areas extending radially outwardly from said central axis and, except for said roughened surface, tapering without interruption toward said plane; and
   (c) a central post extending from said body surface along said central axis.

12. The patellar prosthesis of claim 11, wherein said roughened surface comprises raised areas defining a waffle configuration.

13. The patellar prosthesis of claim 11, wherein said roughened surface comprises grooves defining a waffle configuration.

14. The patellar prosthesis of claim 11, wherein said central post has a plurality of grooves parallel to said central axis.

15. A patellar prosthesis comprising
   (a) a central post extending along a longitudinal axis and
   (b) a body portion extending from said central post, said body portion having
      (i) a first side extending outwardly from said longitudinal axis and tapering away from said central post to an outer peripheral edge, said first side having grooves extending in a direction radial to said longitudinal axis; and
      (ii) a second side having a domed surface, convexly curved throughout, with an apex lying on said longitudinal axis, said apex being spaced axially from said central post further than any other portion of said domed surface.

16. The patellar prosthesis of claim 15, wherein except for said grooves, said first side tapers without interruption.

17. The patellar prosthesis of claim 15, wherein said central post has a plurality of longitudinal grooves.

18. The patellar prosthesis of claim 17, wherein said central post longitudinal grooves intersect said grooves on said first side.

19. The patellar prosthesis of claim 17, wherein said central post longitudinal grooves intersect alternate ones of said grooves on said first side.

* * * * *

UNITED STATES PATENT AND TRADEMARK OFFICE
CERTIFICATE OF CORRECTION

PATENT NO. : 5,197,986
DATED : March 30, 1993
INVENTOR(S) : W. E. Michael Mikhail It is certified that error appears in the above—identified patent and that said Letters Patent is hereby corrected as shown below:

Column 4, line 61, "cute" should be --cut--.

Column 5, line 17, "incircled" should be --encircled--.

Column 5, line 64, after "said" and before "extending" insert --axis--.

Signed and Sealed this

Twenty-eighth Day of December, 1993

Attest:

BRUCE LEHMAN

*Attesting Officer*     *Commissioner of Patents and Trademarks*